(12) United States Patent
Foote et al.

(10) Patent No.: US 7,408,064 B2
(45) Date of Patent: Aug. 5, 2008

(54) CARBAZOLE DERIVATIVES AND THEIR USE AS NPY5 RECEPTOR ANTAGONISTS

(75) Inventors: Kevin Michael Foote, Cheshire (GB); Michael Howard Block, Waltham, MA (US); Wayne Brailsford, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 338 days.

(21) Appl. No.: 10/488,982

(22) PCT Filed: Sep. 9, 2002

(86) PCT No.: PCT/GB02/04109

§ 371 (c)(1),
(2), (4) Date: Nov. 19, 2004

(87) PCT Pub. No.: WO03/022849

PCT Pub. Date: Mar. 20, 2003

(65) Prior Publication Data

US 2005/0065157 A1    Mar. 24, 2005

(30) Foreign Application Priority Data

Sep. 11, 2001    (GB) ................... 0121941.9

(51) Int. Cl.
C07D 471/04    (2006.01)
A61K 31/44    (2006.01)
(52) U.S. Cl. .................... 546/87; 514/292
(58) Field of Classification Search .......... 546/87
See application file for complete search history.

(56) References Cited

U.S. PATENT DOCUMENTS

| | | | |
|---|---|---|---|
| 4,111,850 A | 9/1978 | Kwalwasser | |
| 4,703,107 A | 10/1987 | Monsigny et al. | |
| 4,997,844 A | 3/1991 | Bernstein et al. | |
| 5,223,509 A | * 6/1993 | Evans ................. | 514/292 |
| 5,234,942 A | 8/1993 | Bernstein et al. | |
| 5,254,135 A | 10/1993 | Lang et al. | |
| 6,037,362 A | 3/2000 | Miyoshi et al. | |

FOREIGN PATENT DOCUMENTS

| | | | |
|---|---|---|---|
| DE | 3436281 A1 | | 4/1985 |
| EP | 304223 | * | 2/1989 |
| EP | 342433 A2 | | 11/1989 |
| EP | 381422 A1 | | 8/1990 |
| EP | 179619 B1 | | 9/1990 |
| EP | 434360 | * | 6/1991 |
| EP | 783503 B1 | | 4/1996 |
| EP | 882702 A1 | | 7/1997 |
| EP | 829753 A1 | | 3/1998 |
| EP | 997458 A1 | | 1/1999 |
| EP | 945438 A1 | | 9/1999 |
| JP | 1174077 | | 3/1999 |
| JP | 11130817 | | 5/1999 |
| JP | 11349572 | | 12/1999 |
| WO | WO-92/05170 | | 4/1992 |
| WO | WO-93/07902 | | 4/1993 |
| WO | WO-93/07903 | | 4/1993 |
| WO | WO-93/16694 | | 9/1993 |
| WO | WO-93/18026 | | 9/1993 |
| WO | WO-95/06046 | | 3/1995 |
| WO | WO-96/16542 | | 6/1996 |
| WO | WO-97/19682 | | 6/1997 |
| WO | WO-97/20821 | | 6/1997 |
| WO | WO-98/01417 | | 1/1998 |
| WO | WO-98/35957 | | 8/1998 |
| WO | WO-98/35944 | | 9/1998 |
| WO | WO-98/46590 | | 10/1998 |
| WO | WO-99/03846 | | 1/1999 |
| WO | WO-99/28297 | | 6/1999 |
| WO | WO-99/29660 | | 6/1999 |
| WO | WO-99/32111 | | 7/1999 |
| WO | WO-99/32463 | | 7/1999 |
| WO | WO-99/48868 | | 9/1999 |
| WO | WO-99/48888 | | 9/1999 |
| WO | WO-99/51598 | | 10/1999 |
| WO | WO-99/51600 | | 10/1999 |
| WO | WO-99/55667 | | 11/1999 |
| WO | WO-99/64394 | | 12/1999 |
| WO | WO-00/08015 | | 2/2000 |
| WO | WO-00/20376 | | 4/2000 |
| WO | WO-00/23425 | | 4/2000 |
| WO | WO-00/63171 | | 10/2000 |
| WO | WO-00/69849 | | 11/2000 |
| WO | WO-01/07409 A1 | | 2/2001 |

(Continued)

OTHER PUBLICATIONS

Dorwald Zaragoza, Side Reactions in Organic Synthesis . . . 2005.*

(Continued)

*Primary Examiner*—Rita J Desai

(57) ABSTRACT

The use of a compound of formula (I) in the manufacture of a medicament for the treatment, in a warm-blooded animal, of disorders mediated by the neuropeptide Y5 receptor:

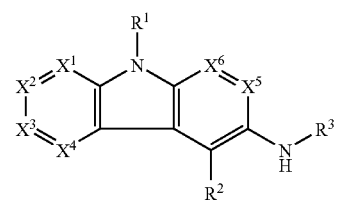

(I)

wherein:
$R_1$, $R_2$, $R_3$ and $X^1$-$X^6$ are as defined within
or a pharmaceutically acceptable salt, prodrug or solvate thereof, is described.

Pharmaceutical compositions, methods and processes for preparation of compounds of formula (I) are also described.

2 Claims, No Drawings

FOREIGN PATENT DOCUMENTS

| WO | WO-01/85730 A1 | 11/2001 |
| WO | WO-01/90120 A2 | 11/2001 |
| WO | WO-02/051806 | 7/2002 |
| WO | WO-03/022849 A1 | 3/2003 |

OTHER PUBLICATIONS

Derwent Abstract XP002193934 (cited for 100249).
Stephenson, L., et al. Synthesis of some Substituted a-Carbolines. J. Chem. Soc. (C) 10, 1355-64 (1970).
Heterocyclic Compounds, 18701-18702 (1961).
Cerri, R., et al. Attivita Analgesica di Derivati di 7-Ammino-2,3-Polimetilenindoli E Loro Congeneri. II Farmaco 43, 113-123 (1988).
Zinnes, H., et al. 1,2-Benzothiazines. 6. 3-Carbamoyl-4-hydrozy-2H-1,2-benzothiazine 1,1-Dioxides as Antiinflammatory Agents. J Med. Chem. 16, vol. 1, 44-48 (1973).
Simionescu, C.I., et al. New Carbazole-Containing Monomers and Polymers. Journal of Polymer Science 17, 2287-2297 (1979).
Harfenist, M., et al. Selective Inhibitors of Monoamine Oxidase 2. Arylamide SAR. J. Med. Chem., 37, 2085-2089 (1994).
Kudo, H., et al. Synthesis of Monoamino and Monohydroxydibenzothiophenes. J. Heterocyclic Chem. 22, 215-219 (1985).
Ohnmacht, C., et al. N-Aryl-3,3,3-trifluoro-2-hydroxy-2-methylpropanamides: Katp Potassium Channel Openers. Modifications on the Western Region. J. Med. Chem. 39, 4592-4601 (1996).
Tye, H., et al. Design, Synthesis and preliminary studies on a novel class of chiral receptor for the recognition of amino acid derivatives. J. Chem. Soc., Perkin Trans. 1, 457-465 (1998).
Chakrabarty, M., et al. An Expedient Synthesis of 5,11-Dimethylindolo [3,2-b]-Carbazole, a Potent Ligand for the Receptor for TCDD. Synthetic Communications 26(16), 3015-3023 (1996).
Lancelot, J., et al. Etude des Reactions de Nitration de L'Acetamido-3 Ethyl-9 Carbazole. J. Heterocyclic Chem. 18, 1281-1285 (1981).
Brunton, R.J., et al. Experiments on the Preparation of Indolocarbazoles. Part IX. The Preparation of 9-Methylindolo (2':3'-1:2) carbazole. J. Chem. Soc., 4783-4785 (1956).
Perche, J.C., et al. Carcinogenic Nitrogen Compounds. Part LXXIV. Skraup and Combes-Beyer Reactions with 3-Aminocarbazoles; a New Route to Pyrido-[3,2'-b]carbazoles. J. Chem. Soc. 2, 260-262 (1972).
Kyziol, J., et al. Bimoecular Reduction of 3-Nitro-9-Ethylcarbazole. Pol J. Chem. 55, 4, 937-940 (1981).
Tye, H., et al. The Synthesis of a Synthetic Receptor via Directed Lithiations of Dibenzofuran and Bibenzothiophene. Synlett 7, 770-772 (1995).
Ponec, R., et al. The Effect of Substitution on Oxidation of Sulphides. Collect Czech. Chem. Commun. 39(8), 2088-2098 (1974).
Brown, R., et al. Some Derivatives of Dibenzothiophene. J. Amer. Chem. Soc. 70, 1748-1749 (1948).
Gilman, H., et al. Some Dialkylaminoalkylamino Derivatives of Dibenzothiophene. J. Am. Chem. Soc. 68, 1514-1515 (1946).
Block, M., et al. Discovery and Optimization of a Series of Carbazole Ureas as DPY5 Antagonists fo rthe Treatment of Obesity. Journal of Medicinal Chemistry 45, No. 16, 3509-23 (2002).
Papamicael, C., et al. Study of the Lithiation of 3-Substituted a-Carbolines A New Route to 3,4-Disubstituted Derivatives. Tett. Lett. 35(24) 4099-4102 (1994).
El-Naggar, A.M., et al. Synthesis of Some New 2- and 3-Substituted Aminoacyl-Aminodibenzothiophene Derivatives. Glas. Hem. Drus. Beograd. 49(4), 151-155 (1984).
Sawicki, E., et al. N-Trifluoroacetyl Derivatives of Carcinogenic Amines. J. Amer. Chem. Soc. 75, 2266-2267 (1953).
Jayalakshmi, S., et al. Proton and Carbon NMR Spectra of 2-Substituted Dibenzothiophenes. Magnetic Resonance in Chemistry 27, 684-686 (1989).
Cordella, A. Ricerche su alcuni coloranti furoil-azoici a sviluppo. Ricerca Sci. 26, 3352-3356 (1956).
Kyziol, J., et al. N-Methyl Derivatives of 3-Aminocarbazole, Pol. J. Chem. 57, 7-8-9, 839-847 (1983).
Kinsley, D.A., et al. The Synthesis and Structure of Some Pyrroloindoles. Journal of the Chemical Society, 1-7 (1958).
J. Soc. Org. Synthet Chem. Japan 12, 29-34 (1954).
Besson, T., et al. Synthesis and Fluorescent Propeties of New Heterobifunctional Fluorescent Probes. Heterocycles 34, No. 2, 273-291 (1992).
Wade, J., et al. Antiallergic Activity of Tetracyclic Derivatives of Quinoline-2-carboxylic Acid. 2. Some Benzothienoquinolinecarboxylic Acids. Journal of Medicinal Chemistry 21, No. 9, 941-949 (1978).
Johnson, J., et al. Synthesis and Antimalarial Effects of [1] Benzothieno [3,2-f] quinazoline-1,3-diamine (1). J. Heterocyclic Chem. 14, 1209-1215 (1977).
Jiang, Z., et al. Photocyclizations of Arylthiofluoroaromatic Compounds: Synthesis of Benzothiophenes. Heterocycles 37, No. 3, 1443-1446 (1994).
Harfenist, M. Prevention of Ames Test Mutagenicity by Chemical Modification in a Series of Monoamine Oxidase Inhibitors. J. Med. Chem. 23, 825-827 (1980).
Tabka, T., et al. Etude de la cytotoxicite in vitro de derives du carbazole I. Nitro et amino-9H-carbazoles. Eur. J. Med. Chem. 23, 119-124 (1988).
Harnois-Pontoni, M., et al. Hydrosoluble Fluorogenic Substrates for Plasmin. Analytical Biochemistry 193, 248-255 (1991).
Eagle, E., et al. Toxicity, Antipyretic and Analgesic Studies on 39 Compounds Including Aspirin, Phenacetin and 27 Derivatives of Carbazole and Tetrahydrocarbazole. Carbazoles and Tetrahydrocarbazoles, 450-457 (1950).
Cerri, R., et al. Nuovi derivati di 7-Ammino-2,3-Polimetilenindoli ad Attivita Antiinflammatoria. II Farmaco Ed. Sc. 43, 91-101 (1987).
Grammaticakis, M., et al. Academie Des Sciences 251, 23, 2728-2731 (1960).
Papamicael, C., et al. Some Applications of the Regioselective Lithiation of a-Carbolines. Heterocycles 47, No. 2 (1998).
Letois, B., et al. Etude de la cytotoxicite in vitro de derives du carbazole III. 3-Amino et 3-nitro-1,4-dimethyl-9H-carbazoles diversement substitues en position 6. European Jouranl of Medicinal Chemistry 25, 775-84 (1990).

* cited by examiner

CARBAZOLE DERIVATIVES AND THEIR USE AS NPY5 RECEPTOR ANTAGONISTS

CROSS-REFERENCE TO RELATED APPLICATIONS

This application is a national stage filing under 35 U.S.C. 371 of International Application No. PCT/GB02/04109, filed Sep. 9, 2002, which claims priority from United Kingdom Patent Application No. 0121941.9, filed Sep. 11, 2001, the specification of which is incorporated by reference herein. International Application No. PCT/GB02/04109 was published under PCT Article 21(2) in English.

This invention relates to compounds which antagonise the interaction between neuropeptide Y (NPY) and the neuropeptide Y5 (NPY-5) receptor sub-type. This invention also relates to processes for the manufacture of NPY-5 receptor antagonists or agonists, pharmaceutically acceptable salts thereof, and to novel pharmaceutical compositions of NPY-5 receptor antagonists or agonists.

NPY is a 36 amino acid polypeptide which is a member of the pancreatic polypeptide family of regulatory peptides with widespread distribution throughout the mammalian system. NPY is the most abundant neuropeptide in the central and peripheral nervous systems and has been shown to have powerful and complex effects on feeding, anxiety, circadian rhythms, reproduction, pituitary-adrenocortical axis function, memory retention, seizures, thermo-regulation, and cardiovascular and gastrointestinal functions. NPY interacts with a heterogeneous population of at least six receptor subtypes, $Y_1$-$Y_6$ which activate adenylate cyclase via a G-protein. For reviews of NPY see: CRC Critical Reviews in Neurobiology. (1988) 4, 97-135; Regulatory Peptides (1996) 62, 1-11.

One of the most striking actions of NPY is induction of feeding in a variety of vertebrate species. Direct injection of NPY into the hypothalamus of satiated rats can increase food intake up to 10-fold over a 4 hour period and NPY is the only known peptide which can cause animals to eat until they are obese. Recent studies on NPY have focused on the identification of the NPY receptor responsible for the regulation of feeding. The NPY-5 receptor has been identified as the receptor most closely matching a proposed appetite receptor. The functional role of this receptor was addressed by receptor blockade studies. Intra-cerebro-ventricular injection of NPY-5 receptor antisense oligodeoxynucleotides prevented the increase in hypothalamic NPY levels during food deprivation and inhibited fasting-induced food intake in rats [Schaffhauser et al (1997) Diabetes 46, 1792-1798]. Thus the NPY-5 receptor is a potential pharmacological target in the modulation of feeding disorders such as obesity. For reviews on the association between NPY and feeding see: Zimanyi et al (1998) Current Pharm Des 4, 349-66; Heinrichs et al (1998) Vitamins and Hormones 54, 51-66.

Obesity is a large and ever expanding problem in affluent societies, which has reached epidemic proportions. According to the US Institute of Medicine, 59% of Americans are clinically obese or at least 20% above their ideal body weight. Obesity is associated with susceptibility to a number of other conditions e.g. non-insulin-dependent diabetes, hypertension, dyslipidaemia and coronary heart disease. These conditions lead to reduction in life expectancy and decreased quality of life. The overall financial burden of obesity is difficult to quantify but it has been estimated that in the US it may account for 6-8% of total healthcare expenditure.

Thus there is need for pharmaceutical agents which have efficacy in the treatment of eating disorders such as obesity, anorexia, bulimia and related disorders. Examples of "related disorders" are diabetes, dyslipidaemia, hypertension and sleep disturbances, particularly diabetes.

Modulation of NPY activity through antagonism at the NPY-5 receptor offers one potential target for pharmacological intervention in these conditions.

Accordingly, the present invention provides a compound of formula (I):

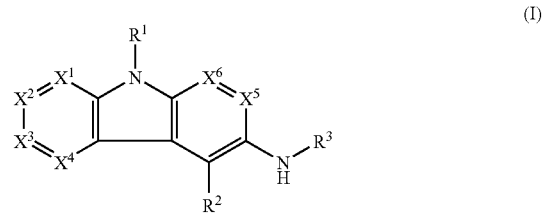

(I)

wherein:
one of $X^1$, $X^2$, $X^3$, $X^4$, $X^5$ and $X^6$ is nitrogen and the others are $CR^4$;

$R^1$ is selected from $C_{1-4}$alkyl, $C_{1-4}$alkanoyl, $C_{1-4}$alkylsulphonyl, N—($C_{1-4}$alkyl)sulphamoyl or N,N—($C_{1-4}$alkyl)$_2$sulphamoyl wherein $R^1$ may be optionally substituted on carbon by one or more $R^5$;

$R^2$ is $C_{1-4}$alkyl;
$R^3$ is —C(O)NR$^6$R$^7$, —C(O)R$^6$ or a group (IA):

(IA)

$R^4$ is independently hydrogen, halo, cyano, hydroxy, trifluoromethyl, trifluoromethoxy, $C_{1-4}$alkyl, N—($C_{1-4}$alkyl)amino, N,N—($C_{1-4}$alkyl)$_2$amino or $C_{1-4}$alkoxy;

$R^5$ is halo, nitro, cyano, hydroxy, trifluoromethyl, trifluoromethoxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl, N,N—($C_{1-4}$alkyl)$_2$sulphamoyl, $C_{1-4}$alkylsulphonylamino, carbocyclyl or heterocyclyl;

$R^6$ and $R^7$ are independently hydrogen, $C_{1-10}$alkyl, $C_{2-10}$alkenyl, $C_{2-10}$alkynyl, carbocyclyl or heterocyclyl wherein $R^6$ and $R^7$ independently may be optionally substituted by one or more $R^9$;

or $R^6$ and $R^7$ together with the nitrogen to which they are attached form a heterocyclic ring optionally substituted on carbon by one or more $R^{10}$; and wherein if said heterocyclic ring contains an —NH— moiety that nitrogen may be optionally substituted by $R^{11}$;

$R^8$ is hydrogen, halo, nitro, cyano, hydroxy, trifluoromethyl, trifluoromethoxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl) amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl, N,N—($C_{1-4}$alkyl)$_2$sulphamoyl, $C_{1-4}$alkylsulphonylamino or (nitrogen-linked heterocyclic ring)carbonyl wherein $R^8$ may be optionally substituted on carbon by on or more $R^{12}$; and wherein if said heterocyclyl contains an —NH— moiety that nitrogen may be optionally substituted by $R^{13}$; and $R^9$ and $R^{10}$ are independently selected from halo, hydroxy, cyano, carbamoyl, ureido, amino, nitro, carboxy, carbamoyl, mercapto, sulphamoyl, $C_{1-4}$alkoxy, $C_{1-4}$alkanoyl, $C_{1-4}$alkanoyloxy, $C_{1-4}$alkanoylamino, $C_{2-6}$alkenyloxycarbonyl, $C_{1-4}$alkoxycarbonyl, heterocyclyl, heterocyclyloxy, heterocyclylcarbonyl, heterocyclyloxycarbonyl, carbocyclyl, carbocyclyloxy, carbocyclylcarbonyl, carbocyclyloxycarbonyl, N—($C_{1-4}$alkyl)amino, N,N—($C_{1-4}$alkyl)$_2$amino, $C_4$alkoxycarbonylamino, N—($C_{1-4}$alkyl)carbamoyl, N,N—($C_{1-4}$alkyl)$_2$carbamoyl, $C_{1-4}$alkylS(O)$_a$ wherein a is 0-2, N—($C_{1-4}$alkyl)sulphamoyl and N,N—($C_{1-4}$alkyl)$_2$sulphamoyl; wherein $R^9$ and $R^{10}$ independently may be optionally substituted on carbon by one or more $R^{14}$; and wherein if said heterocyclyl contains an —NH— moiety that nitrogen may be optionally substituted by $R^{15}$;

$R^{11}$, $R^{13}$ and $R^{15}$ are independently selected from $C_{1-4}$alkyl, $C_{1-4}$alkanoyl, $C_{1-4}$alkylsulphonyl, $C_{1-4}$alkoxycarbonyl, carbamoyl, N—($C_{1-4}$alkyl)carbamoyl, N,N—($C_{1-4}$alkyl)$_2$carbamoyl, benzyl, benzoyl, phenylsulphonyl and phenyl;

$R^{12}$ and $R^{14}$ are independently selected from halo, hydroxy, cyano, carbamoyl, ureido, amino, nitro, carboxy, carbamoyl, mercapto, sulphamoyl, methoxy, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl, N,N-dimethylsulphamoyl, heterocyclyl, heterocyclyloxy, heterocyclylcarbonyl, heterocyclyloxycarbonyl, carbocyclyl, carbocyclyloxy, carbocyclylcarbonyl and carbocyclyloxycarbonyl;

n is 0-3; wherein the values of $R^8$ may be the same or different;

or a pharmaceutically acceptable salt, prodrug or solvate thereof;

with the proviso that said compound is not 4-methyl-6-acetamido-9-acetyl-9H-pyrido[2,3-b]indole.

For the avoidance of doubt, the following naming and numbering scheme is used for the pyridoindoles in this specification:

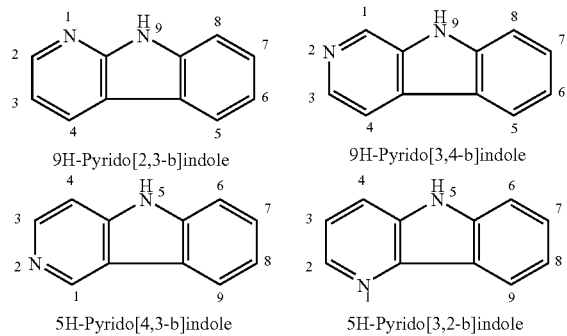

9H-Pyrido[2,3-b]indole    9H-Pyrido[3,4-b]indole
5H-Pyrido[4,3-b]indole    5H-Pyrido[3,2-b]indole In this specification the term "alkyl" includes both straight and branched chain alkyl groups but references to individual alkyl groups such as "propyl" are specific for the straight chain version only. For example, "$C_{1-10}$alkyl" and "$C_{1-4}$alkyl" include propyl, isopropyl and t-butyl. However, references to individual alkyl groups such as 'propyl' are specific for the straight chained version only and references to individual branched chain alkyl groups such as 'isopropyl' are specific for the branched chain version only. A similar convention applies to other radicals, for example "phenyl$C_{1-4}$alkyl" includes phenyl$C_{1-4}$alkyl, benzyl, 1-phenylethyl and 2-phenylethyl. The term "halo" refers to fluoro, chloro, bromo and iodo.

Where optional substituents are chosen from "one or more" groups it is to be understood that this definition includes all substituents being chosen from one of the specified groups or the substituents being chosen from two or more of the specified groups.

A "heterocyclyl" is a saturated, partially saturated or unsaturated, mono or bicyclic ring containing 3-12 atoms of which at least one atom is chosen from nitrogen, sulphur or oxygen, which may, unless otherwise specified, be carbon or nitrogen linked, wherein a —CH$_2$— group can optionally be replaced by a —C(O)— or a ring sulphur atom may be optionally oxidised to form the S-oxides. Preferably a "heterocyclyl" is a saturated, partially saturated or unsaturated, mono or bicyclic ring containing 5 or 6 atoms of which at least one atom is chosen from nitrogen, sulphur or oxygen, which may, unless otherwise specified, be carbon or nitrogen linked, wherein a —CH$_2$— group can optionally be replaced by a —C(O)— or a ring sulphur atom may be optionally oxidised to form S-oxide(s). Examples and suitable values of the term "heterocyclyl" are thiazolidinyl, pyrrolidinyl, pyrrolinyl, 1,1-dioxotetrahydrothienyl, 2-pyrrolidone, 2-oxazolidinone, 4-thiazolidone, morpholino, tetrahydropyranyl, piperidyl, piperazinyl, thiomorpholino, 1,1-dioxothiomorpholino, homopiperazinyl, thienyl, isoxazolyl, imidazolyl, pyrrolyl, thiadiazolyl, isothiazolyl, triazolyl, pyranyl, indolyl, pyrimidyl, pyrazinyl, pyridazinyl, pyridyl, 4-pyridone, quinolyl, 1,3-benzodioxolyl and 1-isoquinolone. Preferably the term "heterocyclyl" refers to pyridyl.

Where $R^6$ and $R^7$ together form a "heterocyclic ring", "heterocyclic ring" is a saturated, partially saturated or fully unsaturated, mono or bicyclic ring containing 4-12 atoms, one atom of which is the nitrogen atom to which $R^6$ and $R^7$ are attached to, and the other atoms are either all carbon atoms or they are carbon atoms and 1-3 heteroatoms chosen from nitrogen, sulphur or oxygen, wherein a —CH$_2$— group can optionally be replaced by a —C(O)—, and a ring sulphur atom may be optionally oxidised to form S-oxide(s). It will be appreciated that where $R^6$ and $R^7$ together with the nitrogen atom to which they are attached form a "heterocyclic ring" this nitrogen atom is not quaternised, i.e. a neutral compound is formed. Suitable values for a "heterocyclic ring" include azetidinyl, morpholino, piperidyl, piperazinyl, pyrrolidinyl, thiomorpholino, pyrrolinyl, homopiperazinyl, pyrrolyl, pyrazolyl, pyrazolinyl, imidazolyl, imidazolinyl, imidazolidinyl, pyrazolidinyl and triazolyl. Preferably a "heterocyclic ring" is morpholino.

A "carbocyclyl" is a saturated, partially saturated or unsaturated, mono or bicyclic carbon ring that contains 3-12 atoms. Preferably "carbocyclyl" is a monocyclic ring containing 5 or 6 atoms or a bicyclic ring containing 9 or 10 atoms. Suitable values for "carbocyclyl" include cyclopropyl, cyclobutyl, cyclopentyl, cyclohexyl, phenyl, naphthyl, tetralinyl or indanyl. Particularly "carbocyclyl" is phenyl.

An example of "$C_{1-4}$alkanoyloxy" is acetoxy. Examples of "$C_{1-4}$alkoxycarbonyl" include methoxycarbonyl, ethoxycarbonyl, n- and t-butoxycarbonyl. Examples of "$C_{1-4}$alkoxycarbonylamino" include methoxycarbonylamino, ethoxycarbonylamino, n- and t-butoxycarbonylamino. Examples of "$C_{1-4}$alkoxy" include methoxy, ethoxy and propoxy. Examples of "$C_{1-4}$alkanoylamino" include formamido, acetamido and propionylamino. Examples of "$C_{1-4}$alkylS(O)$_a$ wherein a is 0 to 2" include methylthio, ethylthio, methylsulphinyl, ethylsulphinyl, mesyl and ethylsulphonyl. Examples of "$C_{1-4}$ alkylsulphonyl" include mesyl and ethylsulphonyl. Examples of "$C_{1-4}$alkylsulphonylamino" include mesylamino and ethylsulphonylamino. Examples of "$C_{1-4}$alkanoyl" include propionyl and acetyl. Examples of "N—($C_{1-4}$ alkyl)amino" include methylamino and ethylamino. Examples of "N,N—($C_{1-4}$alkyl)$_2$amino" include di-N-methylamino, di-(N-ethyl)amino and N-ethyl-N-methylamino. Examples of "$C_{2-10}$alkenyl" and "$C_{2-4}$alkenyl" are vinyl, allyl and 1-propenyl. Examples of "$C_{2-10}$alkynyl" and "$C_{2-4}$alkynyl" are ethynyl, 1-propynyl and 2-propynyl. Examples of "N—($C_{1-4}$alkyl)sulphamoyl" are N-(methyl)sulphamoyl and N-(ethyl)sulphamoyl. Examples of "N,N—($C_{1-4}$alkyl)$_2$sulphamoyl" are N,N-(dimethyl)sulphamoyl and N-(methyl)-N-(ethyl)sulphamoyl. Examples of "N—($C_{1-4}$alkyl)carbamoyl" are methylaminocarbonyl and ethylaminocarbonyl. Examples of "N,N—($C_{1-4}$alkyl)$_2$carbamoyl" are dimethylaminocarbonyl and methylethylaminocarbonyl. Examples of "heterocyclyloxy" are pyridyloxy and thiazolyloxy. Examples of "heterocyclylcarbonyl" are pyrimidylcarbonyl and morpholinocarbonyl. Examples of "heterocyclyloxycarbonyl" are pyrrolidinyloxycarbonyl and pyranyloxycarbonyl. Examples of "carbocyclyloxy" are phenoxy and cyclopropyloxy. Examples of "carbocyclylcarbonyl" are benzoyl and cyclohexylcarbonyl. Examples of "carbocyclyloxycarbonyl" are phenoxycarbonyl and indanyloxycarbonyl. Examples of "(nitrogen-linked heterocyclic ring)carbonyl" are morpholinocarbonyl, imidazolidin-1-ylcarbonyl and pyrazol-1-ylcarbonyl.

A suitable pharmaceutically-acceptable salt of a compound of formula (I) is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

The compounds of the formula (I) may be administered in the form of a prodrug which is broken down in the human or animal body to give a compound of the formula (I). Examples of prodrugs include in vivo hydrolysable esters of a compound of the formula (I).

Various forms of prodrugs are known in the art. For examples of such prodrug derivatives, see:
a) Design of Prodrugs, edited by H. Bundgaard, (Elsevier, 1985) and Methods in Enzymology, Vol. 42, p. 309-396, edited by K. Widder, et al. (Academic Press, 1985);
b) A Textbook of Drug Design and Development, edited by Krogsgaard-Larsen and
H. Bundgaard, Chapter 5 "Design and Application of Prodrugs", by H. Bundgaard p. 113-191 (1991);
c) H. Bundgaard, Advanced Drug Delivery Reviews, 8, 1-38 (1992);
d) H. Bundgaard, et al., Journal of Pharmaceutical Sciences, 77, 285 (1988); and
e) N. Kakeya, et al., Chem Pharm Bull, 32, 692 (1984).

An in vivo hydrolysable ester of a compound of the formula (I) containing a carboxy or a hydroxy group is, for example, a pharmaceutically-acceptable ester which is hydrolysed in the human or animal body to produce the parent acid or alcohol. Suitable pharmaceutically-acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters, for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

An in vivo hydrolysable ester of a compound of the formula (I) containing a hydroxy group includes inorganic esters such as phosphate esters (including phosphoramidic cyclic esters) and α-acyloxyalkyl ethers and related compounds which as a result of the in vivo hydrolysis of the ester breakdown to give the parent hydroxy group/s. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

It is to be understood that, insofar as certain of the compounds of formula (I) defined above may exist in optically active or racemic forms by virtue of one or more asymmetric carbon atoms, the invention includes in its definition any such optically active or racemic form which possesses the property of being an agonist or antagonist at the neuropeptide Y5 receptor. The synthesis of optically active forms may be carried out by standard techniques of organic chemistry well known in the art, for example by synthesis from optically active starting materials or by resolution of a racemic form. Similarly, binding to the neuropeptide Y5 receptor may be evaluated using the standard laboratory techniques referred to hereinafter.

The invention also relates to any and all tautomeric forms of the compounds of the formula (I) that possess neuropeptide Y5 receptor agonist or antagonist activity.

It will also be understood that certain compounds of the present invention may exist in solvated, for example hydrated, as well as unsolvated forms. It is to be understood that the present invention encompasses all such solvated forms which possess the property of interacting with the neuropeptide Y5 receptor.

Further values of $R^1$, $R_2$, $R^1$, $X^1$, $X^2$, $X^3$, $X^4$, $X^5$ and $X^6$ are as follows. Such values may be used where appropriate with any of the definitions, claims or embodiments defined hereinbefore or hereinafter.

In one aspect of the invention $X^1$ is nitrogen.
In another aspect of the invention $X^2$ is nitrogen.
In a further aspect of the invention $X^3$ is nitrogen.
In an additional aspect of the invention $X^4$ is nitrogen.
In one further aspect of the invention $X^5$ is nitrogen.
In another further aspect of the invention $X^6$ is nitrogen.

$R^1$ is selected from $C_{1-4}$alkyl, $C_{1-4}$alkanoyl or $C_{1-4}$alkylsulphonyl wherein $R^1$ may be optionally substituted on carbon by one or more $R^5$; wherein $R^5$ is heterocyclyl.

$R^1$ is selected from $C_{1-4}$alkyl, $C_{1-4}$alkanoyl (substituted by pyridyl) or $C_{1-4}$alkylsulphonyl.

$R^1$ is selected from 3-pyrid-4-ylpropionyl, ethyl, mesyl and isopropyl.

In another aspect of the invention, $R^1$ is $C_{1-4}$alkyl.
$R^1$ is selected from isopropyl.
$R^2$ is methyl or ethyl.
$R^2$ is ethyl.
$R^2$ is methyl.
In one aspect of the invention $R^3$ is —C(O)NR$^6$R$^7$.
In another aspect of the invention $R^3$ is —C(O)R$^6$.
In a further aspect of the invention $R^3$ is a group (IA) (as depicted above).
$R^3$ is —C(O)NR$^6$R$^7$, —C(O)R$^6$ or a group (IA) (as depicted above); wherein:
$R^6$ is $C_{1-10}$alkyl optionally substituted by one or more $R^9$; or
$R^6$ and $R^7$ together with the nitrogen to which they are attached form a heterocyclic ring;
$R^8$ is carbamoyl;
n is 1; and
$R^9$ is heterocyclyl.
$R^3$ is —C(O)NR$^6$R$^7$, —C(O)R$^6$ or a group (IA) (as depicted above); wherein:
$R^6$ is $C_{1-4}$alkyl optionally substituted by one or more $R^9$; or
$R^6$ and $R^7$ together with the nitrogen to which they are attached form morpholino;
$R^8$ is carbamoyl;
n is 1; and
$R^9$ is pyridyl or 1,2,4-triazolyl.
$R^3$ is 3-pyrid-4-ylpropionyl, morpholinocarbonyl, 2-(1,2,4-triazol-1-yl)acetyl, pivaloyl or 6-carbamoylpyridazin-3-yl.
$R^4$ is hydrogen.
$R^8$ is carbamoyl or N,N-dimethylcarbamoyl.
Therefore in another aspect of the invention, there is provided a compound of formula (I) (as depicted above) wherein:
one of $X^1$, $X^2$, $X^3$, $X^4$, $X^5$ and $X^6$ is nitrogen and the others are CH;
$R^1$ is selected from $C_{1-4}$alkyl, $C_{1-4}$alkanoyl or $C_{1-4}$alkylsulphonyl wherein $R^1$ may be optionally substituted on carbon by one or more $R^5$; wherein $R^5$ is heterocyclyl;
$R^2$ is $C_{1-4}$alkyl;
$R^3$ is —C(O)NR$^6$R$^7$, —C(O)R or a group (IA) (as depicted above); wherein:
$R^6$ is $C_{1-10}$alkyl optionally substituted by one or more $R^9$; or
$R^6$ and $R^7$ together with the nitrogen to which they are attached form a heterocyclic ring;
$R^8$ is carbamoyl;
n is 1; and
$R^9$ is heterocyclyl;

or a pharmaceutically acceptable salt, prodrug or solvate thereof.

Therefore in a further aspect of the invention, there is provided a compound of formula (I) (as depicted above) wherein:
one of $X^1$, $X^2$, $X^3$, $X^4$, $X^5$ and $X^6$ is nitrogen and the others are CH;
$R^1$ is selected from 3-pyrid-4-ylpropionyl, ethyl, mesyl and isopropyl;
$R^2$ is ethyl; and
$R^3$ is 3-pyrid-4-ylpropionyl, morpholinocarbonyl, 2-(1,2,4-triazol-1-yl)acetyl, pivaloyl or 6-carbamoylpyridazin-3-yl;

or a pharmaceutically acceptable salt, prodrug or solvate thereof;

In another aspect of the invention, preferred compounds of the invention are any one of the Examples or a pharmaceutically acceptable salt, prodrug or solvate thereof.

Further aspects of the invention are those which relate to the compound of formula (I) or a pharmaceutically acceptable salt thereof.

Another aspect of the present invention provides a process for preparing a compound of formula (I) or a pharmaceutically acceptable salt or an in vivo hydrolysable ester thereof which process (wherein $R^1$, $R^2$, $R^3$, $X^1$, $X^2$, $X^3$, $X^4$, $X^5$ and $X^6$ are, unless otherwise specified, as defined in formula (I)) comprises of:

Process a): for compounds of formula (I) wherein $R^3$ is —C(O)R$^6$; reacting an amine of formula (II):

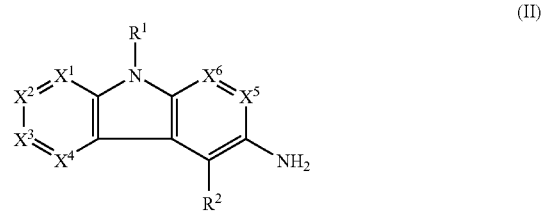

(II)

with an acid of formula (III):

(III)

or an activated derivative thereof, or

Process b): for compounds of formula (I) wherein $R^3$ is —C(O)NR$^6$R$^7$; by reacting a compound of formula (IV):

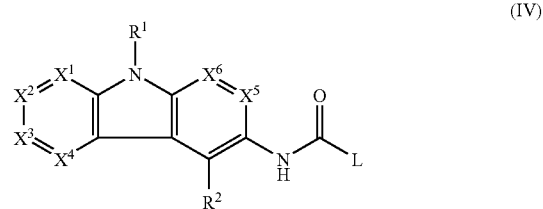

(IV)

wherein L is a displaceable group; with an amine of formula (V):

HNR$^6$R$^7$  (V)

Process c): for compounds of formula (I) wherein $R^3$ is —C(O)NR$^6$R$^7$; reacting a compound of formula (II) with a compound of formula (VI):

(VI)

Process d): for compounds of formula (I) wherein $R^3$ is —C(O)NR$^6$R$^7$ and one of $R^6$ and $R^7$ is hydrogen; reacting a compound of formula (II) with an isocyanate of formula (VII):

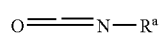

wherein $R^a$ is $R^6$ or $R^7$ not equal to hydrogen;

Process e): for compounds of formula (I) wherein $R^3$ is a group of formula (IA); reacting an amine of formula (II) with a pyridazine of formula (VIII):

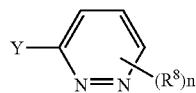
(VIII)

wherein Y is a displaceable group;
Process f): reacting a compound of formula (IX):

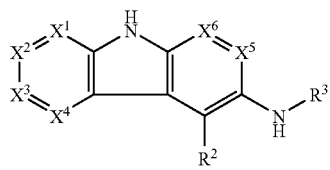
(IX)

with a compound of formula (X):

$R^1$-Z       (X)

wherein Z is a displaceable group or when $R^1$ is $C_{1-4}$alkanoyl Z may be hydroxy;
Process g): for compounds of formula (I) wherein $R^3$ is —C(O)$NR^6R^7$; by reacting a compound of formula (XI):

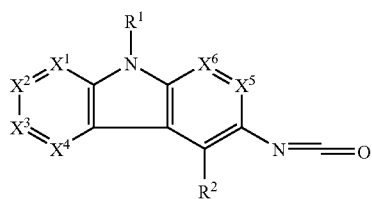
(XI)

with an amine of formula (V);
and thereafter if necessary:
i) converting a compound of the formula (I) into another compound of the formula (I);
ii) removing any protecting groups;
iii) forming a pharmaceutically acceptable salt or in vivo hydrolysable ester.

L is a displaceable group. Suitable values for L are phenols for example p-nitrophenol or penta-fluorophenol.

Y is a displaceable group. A suitable values for Y is halo, for example chloro or bromo.

Specific reaction conditions for the above reactions are as follows.

Process a) Amines of formula (II) and acids of formula (III) may be coupled together in the presence of a suitable coupling reagent. Standard peptide coupling reagents known in the art can be employed as suitable coupling reagents, or for example carbonyldiimidazole and dicyclohexyl-carbodiimide, optionally in the presence of a catalyst such as dimethylaminopyridine or 4-pyrrolidinopyridine, optionally in the presence of a base for example triethylamine, pyridine, or 2,6-di-alkyl-pyridines such as 2,6-lutidine or 2,6-di-tert-butylpyridine. Suitable solvents include dimethylacetamide, dichloromethane, benzene, tetrahydrofuran and dimethylformamide. The coupling reaction may conveniently be performed at a temperature in the range of −40 to 40° C.

Suitable activated acid derivatives include acid halides, for example acid chlorides, and active esters, for example pentafluorophenyl esters. The reaction of these types of compounds with amines is well known in the art, for example they may be reacted in the presence of a base, such as those described above, and in a suitable solvent, such as those described above. The reaction may conveniently be performed at a temperature in the range of −40 to 40° C.

The amines of formula (II) and acids of formula (III) are commercially available or they are known compounds or they are prepared by processes known in the art, see for example those processes described in the examples for preparation of compounds of formula (II).

Process b) Compounds of formula (IV) and amines of formula (V) may be reacted together in the presence of a suitable base, for example triethylamine, pyridine, or 2,6-di-alkyl-pyridines such as 2,6-lutidine or 2,6-di-tert-butylpyridine, or excess (V), in a suitable solvent such as dichloromethane, ethyl acetate or tetrahydrofuran. The reaction may conveniently be performed at a temperature in the range of −40 to 50° C.

The compounds of formula (IV) may be prepared from amines of formula (II) by standard processes known in the art. Compounds of formula (V) are commercially available or they are known compounds or they are prepared by processes known in the art.

Process c) Compounds of formula (II) and compounds of formula (VI) may be reacted in the presence of a base, such as those described above, in a suitable solvent, such as dichloromethane, toluene or tetrahydrofuran. The reaction may conveniently be performed at a temperature in the range of −40 to 100° C.

Compounds of formula (VI) are commercially available or they are known compounds or they are prepared by processes known in the art.

Process d) Compounds of formula (II) and compounds of formula (VII) may be reacted in the presence of a suitable solvent, such as toluene, dichloromethane or tetrahydrofuran. Compounds of formula (VII) are commercially available or they are known compounds or they are prepared by processes known in the art.

Process e) Compounds of formula (II) and compounds of formula (VIII) may be reacted in the presence of a suitable solvent, such as toluene, dichloromethane, ethanol or tetrahydrofuran. The reaction may conveniently be performed at a temperature in the range of 25 to 100° C., preferably at or near reflux and optionally in the presence of a palladium catalyst.

Compounds of formula (VIII) are commercially available or they are known compounds or they are prepared by processes known in the art.

Process f) Compounds of formula (IX) and compounds of formula (X) may be reacted together in the presence of a suitable base, for example sodium hydride, potassium hexamethyldisilazane, triethylamine, pyridine, or 2,6-di-alkyl-pyridines such as 2,6-lutidine or 2,6-di-tert-butylpyridine, in a suitable solvent such as dichloromethane, ethyl acetate or tetrahydrofuran. The reaction may conveniently be performed at a temperature in the range of 25° C. to reflux. When $R^1$ is $C_{1-4}$alkanoyl and Z is hydroxy compounds of formula (IX) and compounds of formula (X) may be reacted together in conditions such as those described in Process a) above.

Compounds of formula (IX) may be prepared by the procedures described for the preparation of compounds of formula (I), but wherein $R^1$ is hydrogen. The person skilled in the art may also be aware if a protecting group for this nitrogen would be necessary. Therefore compounds of formula (IX) may also be prepared by deprotecting a compound of formula (I) wherein $R^1$ is a nitrogen protecting group.

Compounds of formula (X) are commercially available or they are known compounds or they are prepared by processes known in the art.

Process g) Compounds of formula (XI) and amines of formula (V) may be reacted together under similar conditions to those described in Process d).

Compounds of formula (XI) may be prepared according to Scheme 1:

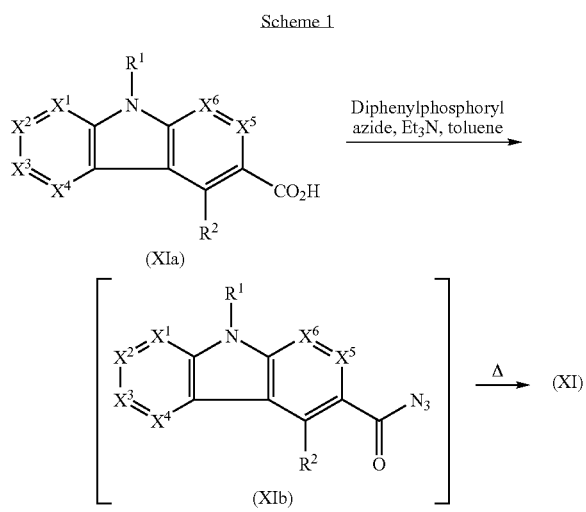

Compounds of formula (XIa) are commercially available or they are known compounds or they are prepared by processes known in the art, see for example the processes described in the examples.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halo group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl. The reader is referred to Advanced Organic Chemistry, $4^{th}$ Edition, by Jerry March, published by John Wiley & Sons 1992, for general guidance on reaction conditions and reagents.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

Biological Assays

The activity of compounds of the invention was measured in a neuropeptide Y5 receptor binding assay as follows. Compounds were also tested in binding assays for the neuropeptide Y$_1$ and neuropeptide Y$_2$ receptors. Activity against these 2 receptors is contraindicated for a neuropeptide Y5 antagonist.

a) Expression of Human Neuropeptide Y5 Receptor in High 5™ insect cells.

High 5™ insect cells were obtained from Invitrogen (catalogue No B855-02) and stored in liquid nitrogen. Cells were revived from liquid nitrogen storage and grown at 28° C. in 100 ml ExCell 405 (JRH Biosciences) serum free medium in a 250 ml conical flask (Corning) agitated at 140 rpm in an Innova 4330 orbital shaker (New Brunswick Scientific). Cultures were routinely sub-cultured every 3-4 days.

High 5™ insect cells were transfected with the human NPY5 receptor as follows. PCR primers were designed against the huNPY5 receptor sequence, Genbank Accession Number U56079 [Gerald et. al. (1996) Nature 382, 168-171], but starting at base 56 through to base 1393, to express the protein 10 amino acid residues shorter at the amino terminal end [see Borowsky et. al. (1998) Regulatory Peptides 75-76, 45-53]. These primers were used to amplify the huNPY5 receptor from human placenta genomic DNA by PCR. This was then sub-cloned into pZERO2 (obtained from Invitrogen) for sequencing and re-cloned into pFASTBAC1 (obtained from GIBCO BRL Life Technologies) for expression. Human NPYr was isolated from pZERO2 on BamHI fragment and sub-cloned into pFastbac1 on BamHI restriction site. The junctions were sequenced to ensure correct prior to expression.

A baculovirus containing the pFASTBAC1 was then generated using the Bac-to-Bac™ baculovirus expression system [Anderson et al (1996) FASEB Journal 10(6), 727-726] (obtained from GIBCO BRL Life Technologies) following the protocol supplied with this expression system by GIBCO BRL Life Technologies.

High 5™ insect cells were infected with the baculovirus to transfect the cells with the human neuropeptide Y5 receptor as follows: Batches were grown for membrane preparation by inoculating 5 L of ExCell 405™ medium in a 7 L Bioreactor (FT-Applikon) with 1.75×10$^9$ mid log High 5™ cells. After 2-3 days growth at 28° C. the mid log culture was infected with Baculovirus expressing the human NPY5 receptor at a multiplicity of infection (MOI) of 1.0. Cells (typically 1×10$^{10}$) were harvested 48 hours post infection by centrifugation (Heraeus Omnifuge 2.0RS 30 min, 296 g, 4° C.) and flash frozen in liquid nitrogen for storage at −80° C.

b) Membrane Preparation Procedure

The following buffer was prepared daily and stored at 4° C. 50 mM Tris HCl pH 7.4, 5 mM EDTA and 10% w.v. sucrose. A protease inhibitor cocktail (Boehringer Mannheim) was added to both buffers according to the manufacturers instruction. Cells were thawed rapidly in three times their packed cell volume of hypotonic buffer (3:1 mix of water and buffer) and lysed routinely on ice using five Vibra Cell Sonicator (Sonics and Materials Inc.) bursts of ten seconds for the High 5™ insect cells. The cell lysate (typically 10-15 ml) was carefully loaded onto a 10 ml 41% sucrose cushion which was topped off with lysis buffer and spun at 150,000 g for 1 hour at 4° C. in a Beckman Optima LE-80K Ultracentrifuge. The membrane fraction was carefully removed from the interphase and diluted at least four fold with lysis buffer. The membrane pellets were recovered by centrifugation at 150,000 g for 20 min at 4° C. in a Beckman Optima LE-80K Ultracentrifuge and re-suspended at 5×10$^7$ cell equivalents per ml. The re-suspended membranes were divided into working aliquots, routinely 1 ml, flash frozen in liquid nitrogen and stored frozen at −80° C. until use.

Prior to use the 1 ml High 5™ membranes were thawed and resuspended in 8 ml binding buffer (see below). Membranes are used at approximately 7 μg/ml of protein per incubate.

c) Neuropeptide Y5 Receptor Binding Assay

The following reagents were used:
Binding buffer: 50 mM HEPES, 2.5 mM CaCl$_2$, 1 mM MgCl$_2$, 0.5% BSA, pH=7.4
Binding wash buffer: 50 mM HEPES, 2.5 mM CaCl$_2$, 1 mM MgCl$_2$, 0.5M NaCl, 0.5% BSA, pH=7.4
Unifilter GFC filter plates: 50 μl of 0.5% polyethyleneimine was added to each well and left to equilibrate for four hours before use
Incubation plates: 96 well polypropylene plates, siliconised prior to use
Test Compounds: Compounds were dissolved in DMSO at a concentration of 1 mM.
Final concentration of DMSO in the assay did not exceed 1%.
Peptide PYY (pancreatic polypeptide Y)—10 μM stock solution in binding buffer.
$^{125}$I PYY—10 μCi/ml stock solution, diluted 1:10 dilution, into binding buffer.

Assays were performed in 96 well microtitre plates. 10 μl of diluted test compound was added to each well of a plate, followed by 80 μl of membranes and 10 μl of radiolabelled $^{125}$I PYY (0.01 μCi per well). Total and non-specific binding controls were included in each plate. The non-specific binding wells received 10 μl of Peptide PYY from the 10 μM stock solution, whilst the total binding wells received 10 μl of binding buffer. For each assay, a duplicate dose response of peptide PYY was included, top concentration 1 μM.

The plates were incubated for two hours at room temperature with mixing, and then filtered onto the pre-treated filter plates. The incubation plates were washed twice with 150 μl of cold binding wash buffer per well, then the filter plates were further washed with approximately 2.5 ml per well. The filter plates were dried overnight at room temperature, the bottoms were sealed, and 20 μl of Scintillant (Microscint 40, Canberra Packard) was added to each well. The tops of the plates were sealed and the plates were counted for 1 minute on a protocol set up for $^{125}$I on a 96 well plate liquid scintillation counter (Top Count, Canberra Packard).

Compounds were considered to be active if they inhibited the binding by more than 50% at a concentration of 10 μM. Dose responses were carried out on all compounds found to be active (8 point curves in duplicate).

Although the pharmacological properties of the compounds of the formula (I) vary with structural change as expected, in general compounds of the formula (I) possess an IC$_{50}$ in the above test in the range, for example, 0.0002 to 200 μM.

In order to use a compound of the formula (I) or a pharmaceutically acceptable salt, prodrug or solvate thereof, for the therapeutic treatment (including prophylactic treatment) of mammals including humans, it is normally formulated in accordance with standard pharmaceutical practice as a pharmaceutical composition.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for administration by insufflation may be in the form of a finely divided powder containing particles of average diameter of, for example, 30 μm or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the formula (I) will naturally vary according to the nature and severity of the conditions, the age and sex of the animal or patient and the route of administration, according to well known principles of medicine.

In using a compound of the formula (I) for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred, particularly in tablet form. Typically, unit dosage forms will contain about 1 mg to 500 mg of a compound of this invention.

The compounds of this invention may be used in combination with other drugs and therapies used in the treatment of disease states which would benefit from antagonism at the neuropeptide Y5 receptor. For example, the compounds of the formula (I) could be used in combination with drugs and therapies used in the treatment of eating disorders.

If formulated as a fixed dose such combination products employ the compounds of this invention within the dosage range described herein and the other pharmaceutically-active agent within its approved dosage range. Sequential use is contemplated when a combination formulation is inappropriate.

Although the compounds of the formula (I) are primarily of value as therapeutic agents for use in a warm-blooded animal, such as a human being, they are also useful whenever it is required to antagonise binding at the neuropeptide Y5 receptor. Thus, they are useful as pharmacological standards for use in the development of new biological tests and in the search for new pharmacological agents.

According to a further aspect of the invention there is provided a pharmaceutical composition which comprises a compound of the formula (I) or a pharmaceutically acceptable salt, prodrug or solvate thereof, in association with a pharmaceutically acceptable diluent or carrier.

According to one feature of the invention there is provided the use of a compound of formula (I), or a pharmaceutically acceptable salt, prodrug or solvate thereof, as a medicament.

According to a further aspect of the present invention there is provided a compound of the formula (I), or a pharmaceutically acceptable salt, prodrug or solvate thereof, for use in a Method of treatment of a warm-blooded animal by therapy.

According to another aspect of the invention there is provided a pharmaceutical composition comprising a compound of formula (I), or a pharmaceutically acceptable salt, prodrug or solvate thereof, in association with a pharmaceutically acceptable diluent or carrier for the treatment of disorders mediated by the neuropeptide Y5 receptor in a warm-blooded animal in need of such treatment.

Examples of "disorders mediated by the neuropeptide Y5 receptor" are eating disorders. Examples of eating disorders include obesity, bulimia or anorexia. Further examples of eating disorders include: obesity and related disorders, bulimia or anorexia. Examples of "related disorders" are diabetes, dyslipidaemia, hypertension and sleep disturbances. Preferably "related disorders" refers to diabetes.

According to a further aspect of the invention there is provided a pharmaceutical composition comprising a compound of formula (I), or a pharmaceutically acceptable salt, prodrug or solvate thereof, in association with a pharmaceutically acceptable diluent or carrier for the treatment of eating disorders in a warm-blooded animal.

According to a further aspect of the invention there is provided a pharmaceutical composition comprising a compound of formula (I), or a pharmaceutically acceptable salt, prodrug or solvate thereof, in association with a pharmaceutically acceptable diluent or carrier for use in promoting weight loss.

Preferably promoting weight loss would refer to promoting weight loss in a warm-bloodied animal. Preferably a warm-blooded animal is man.

According to a further aspect of the invention there is provided the use of a compound of formula (I), or a pharmaceutically acceptable salt, prodrug or solvate thereof, in the manufacture of a medicament for the treatment of eating disorders in a warm-blooded animal.

According to another feature of the invention there is provided the use of a compound of formula (I), or a pharmaceutically acceptable salt, prodrug or solvate thereof, in the manufacture of a medicament for promoting weight loss.

According to a further aspect of the invention there is provided a Method of treatment, in a warm-blooded animal, of eating disorders, comprising administering a therapeutically effective amount of a compound of formula (I), or a pharmaceutically acceptable salt, prodrug or solvate thereof.

According to a further aspect of the invention there is provided a Method of promoting weight loss, comprising administering a therapeutically effective amount of a compound of formula (I), or a pharmaceutically acceptable salt, prodrug or solvate thereof.

For the pharmaceutical compositions, methods of treatment and use aspects of this invention, it is to be understood that compounds of formula (I) include the compound 4-methyl-6-acetamido-9-acetyl-9H-pyrido[2,3-b]indole and pharmaceutically acceptable salts, prodrugs and solvates thereof.

EXAMPLES

The invention will now be illustrated by the following non-limiting examples in which, unless stated otherwise:

(i) temperatures are given in degrees Celsius (° C.); operations were carried out at room or ambient temperature, that is, at a temperature in the range of 18-25° C.;

(ii) organic solutions were dried over anhydrous magnesium sulphate; evaporation of solvent was carried out using a rotary evaporator under reduced pressure (600-4000 Pascals; 4.5-30 mmHg) with a bath temperature of up to 60° C.;

(iii) chromatography means flash chromatography on silica gel (Merck Keiselgel ART 9385); thin layer chromatography (TLC) was carried out on silica gel plates; where a "Bond Elut" column is referred to, this means a column containing 20 g of silica, the silica being contained in a 70 ml disposable syringe and supported by a porous disc of 54 Å pore size, obtained from International Sorbent Technology under the name "ISOLUTE"; "ISOLUTE" is a registered trade mark;

(iv) in general, the course of reactions was followed by TLC and reaction times are given for illustration only;

(v) final products had satisfactory proton nuclear magnetic resonance (NMR) spectra and/or mass spectral data;

(vi) yields are given for illustration only and are not necessarily those which can be obtained by diligent process development; preparations were repeated if more material was required;

(vii) when given, NMR data is in the form of delta values for major diagnostic protons, given in parts per million (ppm) relative to tetramethylsilane (TMS) as an internal standard, determined at 300 MHz using perdeuterio dimethyl sulphoxide (DMSO-$d_6$) as solvent unless otherwise indicated; s, singlet; d, doublet; dd, double doublet; t, triplet; tt, triple triplet; q, quartet; tq, triple quartet; m, multiplet; br, broad;

(viii) chemical symbols have their usual meanings; SI units and symbols are used;

(ix) solvent ratios are given in volume:volume (v/v) terms; and (x) mass spectra were run with an electron energy of 70 electron volts in the chemical ionization (CI) mode using a direct exposure probe; where indicated ionization was effected by electron impact (EI), fast atom bombardment (FAB) or electrospray (ES); values for m/z are given; generally, only ions which indicate the parent mass are reported; unless otherwise stated the value for (M+H)$^+$ is quoted;

(xi) unless stated otherwise compounds containing an asymmetrically substituted carbon and/or sulphur atom have not been resolved;

(xii) where a synthesis is described as being analogous to that described in a previous example the amounts used are the millimolar ratio equivalents to those used in the previous example;

(xvi) the following abbreviations have been used:

| | |
|---|---|
| EDAC | 1-[3-(dimethylamino0propyl]-3-ethylcarbodiimide hydrochloride; |
| DMAP | 4-dimethylaminopyridine; |
| DMF | N,N-dimethylformamide; |
| DCM | dichloromethane; |
| MeOH | methanol; |
| MeCN | acetonitrile; |
| TFA | trifluoroacetic acid; |
| EtOAc | ethyl acetate; |
| EtOH | ethanol; and |
| ether | diethyl ether. |

Example 1

3-(3-Pyrid-4-ylpropionamido)-4-ethyl-9-isopropyl-9H-pyrido[3,4-b]indole

EDAC (0.035 g, 0.18 mmol) was added to a solution of 3-amino-4-ethyl-9-isopropyl-9H-pyrido[3,4-b]indole (Method 5; 0.03 g, 0.12 mmol), DMAP (0.007 g, 0.06 mmol) and 3-(pyridin-4-yl)propanoic acid (Method 6; 0.027 g, 0.18 mmol) in DMF (10 ml). The mixture was stirred at room temperature for 18 hours. The solvent was removed in vacuo and the residue partitioned between dichloromethane and a saturated solution of sodium bicarbonate. The organic layer was separated, washed with brine, dried over magnesium sulphate and then evaporated to dryness in vacuo. The crude product was purified by flash chromatography eluting over a gradient of 0-10% MeOH in DCM. NMR (CDCl$_3$) 8.72 (s, 1H), 8.51 (m, 2H), 8.19 (d, 1H), 7.59 (d, 2H), 7.47 (s, 1H), 7.29 (m, 1H), 7.20 (m, 2H), 5.05 (m, 1H), 3.12 (m, 4H), 2.78 (m, 2H), 1.73 (d, 6H), 1.31 (t, 3H); m/z 388.

Preparation of Starting Materials

The starting materials for the Examples above are either commercially available or are readily prepared by standard methods from known materials. For example the following reactions are illustrations but not limitations of the preparation of some of the starting materials used in the above reactions.

Method 1

3-Ethoxycarbonyl-9-isopropyl-9H-pyrido[3,4-b]indole

Potassium bis-(trimethylsilyl)amide (5.48 g, 27.5 mmol) was added portionwise over 5 minutes under an atmosphere of argon to a stirred solution of 3-ethoxycarbonyl-9H-pyrido[3,4-b]indole (6 g, 25 mmol) in THF (60 ml) at 0° C. After 1 hour, 2-bromopropane (19 ml, 0.2 mol) was added dropwise over 10 minutes at room temperature and the reaction mixture was then heated to 60° C. for 18 hours. The mixture was concentrated in vacuo and the residue was dissolved in EtOAc. The solution was washed with water and then brine. The organic phase was separated, dried, filtered and concentrated in vacuo. The crude product was purified by flash eluting over a gradient of 0-70% EtOAc in isohexane. The product was obtained as a yellow solid (2.91 g) after evaporation of the appropriate fractions. NMR (300 MHz) 9.21 (s, 1H), 8.92 (s, 1H), 8.41 (d, 1H), 7.86 (d, 1H), 7.62 (t, 1H), 7.33 (t, 1H), 5.28 (m, 1H), 4.37 (q, 2H), 1.69 (d, 6H), 1.37 (t, 3H); m/z 283.5.

Method 2

3-Carboxy-9-isopropyl-9H-pyrido[3,4-b]indole

A solution (1 mol dm$^{-3}$) of sodium hydroxide (21 ml, 21 mmol) was added over 10 minutes to a stirred solution of 3-ethoxycarbonyl-9-isopropyl-9H-pyrido[3,4-b]indole (Method 1; 2.9 g, 10.3 mmol) in a MeOH/water mix (100 ml 2:1 v/v), and the mixture was allowed to stir for 20 hours at room temperature. MeOH was removed in vacuo and the mixture acidified by the addition of HCl (1 mol dm$^{-3}$). The precipitate was filtered, washed with water and dried under vacuum at 65° C. for 2 hours to give a light yellow solid (2.15 g). NMR (300 MHz) 9.19 (s, 1H), 8.91 (s, 1H), 8.41 (d, 1H), 7.85 (d, 1H), 7.62 (t, 1H), 7.31 (t, 1H), 5.26 (m, 1H), 1.66 (d 6H); m/z 255.

Method 3

3-Carboxy-4-ethyl-9-isopropyl-9H-pyrido[3,4-b]indole n-Butyllithium (2.5 M in hexanes, 3.2 ml, 8 mmol) and 3-carboxy-9-isopropyl-9H-pyrido[3,4-b]indole (Method 2; 504 mg, 2 mmol) were added to a solution of 2,2,6,6-tetramethyl piperidine (1.01 ml, 6 mmol) in THF (15 ml) at −50° C. The mixture was allowed to stir for 30 minutes warming to 0° C. Methyl iodide (0.15 ml, 2.4 mmol) was then added in a single portion and the mixture was left at 0° C. for a further 30 minutes and at room temperature for a further 16 hours. The mixture was concentrated in vacuo and the residue was dissolved in DCM. The solution was washed with 1 M HCl and then with water. The organic phase was separated, dried and concentrated in vacuo. The crude product was purified by preparative HPLC eluting over a gradient of 20-90% MeCN in water (0.1% TFA). The product was obtained as a yellow solid (190 mg) after evaporation of the appropriate fractions. NMR (300 MHz) 9.16 (s, 1H), 8.39 (d, 1H), 8.01 (d, 1H), 7.72 (t, 1H), 7.43 (t, 1H), 5.39 (m, 1H), 3.60 (q, 2H), 1.67 (d, 6H), 1.38 (t, 3H).

Method 4

3-[2-(Trimethylsilyl)ethoxycarbonylamino]-4-ethyl-9-isopropyl-9H-pyrido[3,4-b]indole Diphenyl phosphoryl azide (0.15 ml, 0.69 mmol) was added to a stirred solution of 3-carboxy-4-ethyl-9-isopropyl-9H-pyrido[3,4-b]indole (Method 3; 186 mg, 0.66 mmol) and triethylamine (0.1 ml, 0.69 mmol) in toluene (5 ml). The mixture was heated to 80° C. for 2 hours. 2-Trimethylsilylethanol (0.19 ml, 1.32 mmol) was then added and the mixture was allowed to stir for a further 6 hours at 80° C. The mixture was concentrated in vacuo and the residue was dissolved in EtOAc, washed with 1M NaOH and then with water. The organic phase was separated, dried and evaporated in vacuo. The crude product was purified by flash chromatography eluting over a gradient of 0-5% MeOH in DCM. The product was obtained as a light brown oil (84 mg) after evaporation of the appropriate fractions. NMR (300 MHz, CDCl$_3$) 8.70 (s, 1H), 8.16 (d, 1H), 7.54 (m, 2H), 7.21 (m, 1H), 6.66 (s, 1H), 4.98 (m, 1H), 4.22 (m, 2H), 3.25 (q, 2H), 1.69 (d, 6H), 1.38 (t, 3H), 1.01 (m, 2H).

Method 5

3-Amino-4-ethyl-9-isopropyl-9H-pyrido[3,4-b]indole

Tetrabutylammonium flouride (1M in THF, 5 ml, 5 mmol) was added to 3-[2-(trimethylsilyl)ethoxycarbonylamino]-4-ethyl-9-isopropyl-9H-pyrido[3,4-b]indole (Method 4; 80 mg, 0.2 mmol) and the mixture was heated to 50° C. for 1 hour. The mixture was concentrated in vacuo and the residue was dissolved in DCM and washed with water. The organic phase was separated, dried and evaporated in vacuo. The crude product was purified by flash eluting over a gradient of 0-2.5% MeOH in DCM. The product was obtained as a light brown solid (34 mg) after evaporation of the appropriate fractions. NMR (300 MHz, CDCl$_3$) 8.40 (s, 1H), 8.16 (d, 1H), 7.48 (m, 2H), 7.18 (t, 1H), 4.91 (m, 1H), 3.13 (q, 2H), 1.69 (d, 6H), 1.40 (t, 3H); m/z 255.

Method 6

3-(Pyridin-4-yl)propanoic acid

To a solution of ethyl 3-pyridin-4-ylpropanoate (Method 7; 103.1 g, 576 mmol) in water (400 ml) and EtOH (20 ml) at room temperature was added potassium hydroxide (60 g, 1600 mmol). After 18 hours hydrochloric acid (100 ml) was added to give a white solid 62.8 g (73%). NMR (300 MHz) 8.38 (d, 2H), 7.21 (d, 2H), 2.70 (t, 2H), 2.52 (t, 2H); m/z 152.2.

Method 7

Ethyl 3-pyridin-4-ylpropanoate

Ethyl (E)-3-pyridin-4-ylprop-2-enoate (Method 8; 102.3 g, 576 mmol) in MeOH (300 ml) was hydrogenated using palladium on carbon 5% (9.0 g) under atmospheric pressure hydrogen for 72 hours. The catalyst was filtered off through diatomaceous earth and the filtrate concentrated to give a yellow oil. Yield 103.1 g (99%). NMR (300 MHz, CDCl$_3$) 8.50 (d, 2H), 7.15 (d, 2H), 4.12 (q, 2H), 2.95 (t, 2.64 (t, 2H), 1.21 (t, 3H); m/z 180.4.

Method 8

Ethyl (E)-3-pyridin-4-ylprop-2-enoate

To a solution of 4-pyridinecarboxaldehyde (67 ml, 700 mmol) and triethyl phosphonacetate (152 ml, 770 mmol) in THF (200 ml) at room temperature was added lithium hydroxide (32.4 g, 770 mmol). After 18 hours ether (500 ml) was added and the solution was washed with sodium hydrogen carbonate, brine and concentrated to give a white solid. Yield 102.1 g (83%). NMR (300 MHz) 8.62 (d, 2H), 7.60 (d, 1H), 7.35 (d, 2H), 6.59 (d, 1H), 4.30 (q, 2H), 1.35 (t, 3H); m/z 178.3.

Example 2

The following illustrate representative pharmaceutical dosage forms containing the compound of formula (I), or a pharmaceutically acceptable salt, prodrug or solvate thereof (hereafter compound X), for therapeutic or prophylactic use in humans:

| (a): Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b): Tablet II | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c): Tablet III | mg/tablet |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d): Capsule | mg/capsule |
|---|---|
| Compound X | 10 |
| Lactose Ph.Eur | 488.5 |
| Magnesium stearate | 1.5 |

-continued

| (e): Injection I | (50 mg/ml) |
|---|---|
| Compound X | 5.0% w/v |
| 1M Sodium hydroxide solution | 15.0% v/v |
| 0.1M Hydrochloric acid | (to adjust pH to 7.6) |
| Polyethylene glycol 400 | 4.5% w/v |
| Water for injection | to 100% |

| (f): Injection II | 10 mg/ml |
|---|---|
| Compound X | 1.0% w/v |
| Sodium phosphate BP | 3.6% w/v |
| 0.1M Sodium hydroxide solution | 15.0% v/v |
| Water for injection | to 100% |

| (g): Injection III | (1 mg/ml, buffered to pH6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection | to 100% |

Note
The above formulations may be obtained by conventional procedures well known in the pharmaceutical art. The tablets (a)-(c) may be enteric coated by conventional means, for example to provide a coating of cellulose acetate phthalate.

What is claimed is:

1. A compound of Formula (I):

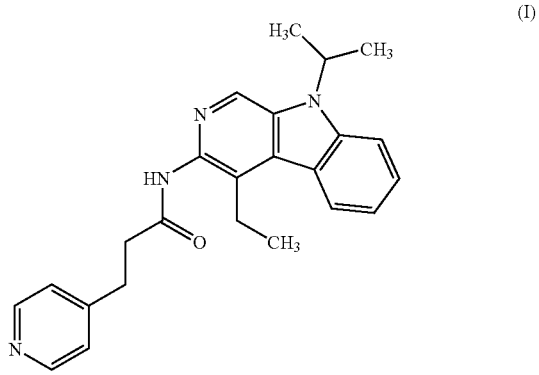

or a pharmaceutically acceptable salt thereof.

2. A composition, comprising the compound of claim 1, or a pharmaceutically acceptable salt thereof, in admixture with a pharmaceutically acceptable diluent or carrier.

* * * * *